United States Patent [19]

Vyas

[11] Patent Number: 4,483,793

[45] Date of Patent: Nov. 20, 1984

[54] DIMERIC OLIGOPEPTIDES AS HEPTENIC EPITOPIC SITES FOR HEPATITIS

[75] Inventor: Girish N. Vyas, Orinda, Calif.

[73] Assignee: The Regents of the University of California, Berkeley, Calif.

[21] Appl. No.: 432,580

[22] Filed: Oct. 4, 1982

[51] Int. Cl.$^3$ .................. A61K 37/02; A61K 39/29; A61K 39/12; C07G 7/00; C07C 103/52

[52] U.S. Cl. .................. 260/112.5 R; 424/86; 424/89; 424/177

[58] Field of Search .................. 424/85, 86, 88, 89, 424/177; 260/112.5

[56] References Cited

U.S. PATENT DOCUMENTS 4,415,491 11/1983 Vyas .................. 260/112.5 R

*Primary Examiner*—Thomas G. Wiseman
*Assistant Examiner*—Robin Teskin
*Attorney, Agent, or Firm*—Bertram I. Rowland

[57] ABSTRACT

Methods and compositions concerned with the a determinant of hepatitis B antigen, providing immunogens and antibodies. The immunogens can serve as vaccines.

3 Claims, No Drawings

DIMERIC OLIGOPEPTIDES AS HEPTENIC EPITOPIC SITES FOR HEPATITIS

BACKGROUND OF THE INVENTION

1. Field of the Invention

Hepatitis B virus (HBV) infection is a world-wide public health problem causing acute and chronic liver diseases including hepatocellular carcinoma. Hepatitis B surface antigen (HBsAg) isolated from the plasma of chronic carries has been extensively studied for immunochemical specificity of the physiologically predominant antigenic determinant a, common to all serotypes of HBsAg, and other subtype specific determinants d/y or w/r, there being a total of ten different serotypes of which four are major. The amino acid sequence of the virally coded HBsAg structural protein of 25,000 daltons has been obtained and the polypeptide sequence associated with the a determinant been defined.

As one outgrowth of this intensive effort is the desire to be able to produce economic, effective, safe vaccines which protect mammalian hosts against the various serotypes of HBV. In developing a vaccine, one wishes to mimic the virulent organism to the greatest degree in the same manner as the virulent organism provokes the natural immunogenic response. At the same time, one wishes to avoid the adverse symptoms resulting from infection. While the determinant site associated with the particular antibodies produced during infection may be only a small portion of a surface protein, the protein may provide the environment and conformation which is specific for the determinant site.

It is, therefore, of great interest to be able to produce relatively small oligopeptides which can serve as haptens to prepare immunogens which provoke a strong immunological response upon injection into a host, so as to act as a vaccine to protect the host from subsequent infection of a microorganism having such a determinant. For hepatitis, it is particularly important to provide for an immunogenic response which produces antibodies specific to the a determinant, so that the host will be immunized against all the serotypes of HBV. It is, therefore, desirable to be able to prepare novel haptenic oligopeptides which can be used for the production of immunogens to be used as vaccines, for the production of antibodies for use in diagnosis or passive immunization or as reagent in diagnostic assays.

2. Description of the Prior Art

Bhatnagar et al., PNAS U.S.A. (1982) 79:4400–4404 describe the HBsAg/adw protein as determined from the gene, various sequences which are shown to be able to compete with the HBsAg for antibodies binding to HBsAg and a list of references providing the historical development of the determination of HBsAg and its determinant sites. See also, Audibert et al., PNAS USA (1982) 79:5042–5046 for a synthetic diphtheria vaccine.

SUMMARY OF THE INVENTION

Novel dimeric oligopeptides are provided as haptens capable of binding with human antibodies specific for the a determinant of HBsAg, for polymerization and/or conjugation to antigens to produce immunogens, which may serve for the production of antibodies or as vaccines, or the oligopeptides and immunogens may be used in diagnostic assays along with the antibodies produced therefrom as reagents.

DESCRIPTION OF THE SPECIFIC EMBODIMENTS

In accordance with the subject invention, novel oligopeptide haptens are provided which mimic the HBsAg a determinant site and, therefore, find use in a wide variety of applications, such as in the preparation of reagents for use in diagnostics, the preparation of antigens which may then be used for the production of antibodies, where the antibodies may find use in diagnostic assays or as vaccines for passive immunization, or the oligopeptides may be polymerized or conjugated to antigens accepted by mammalian hosts for inducing an immune response to provide for protection against infection by HBV.

The oligopeptides of the subject invention will normally have at least about 10 and not more than about 30 (15 members in each leg), usually not more than about 24 (12 members in each leg), and preferably about 18 members (9 members in each leg) of which all need not be amino acids, the predominant number being amino acids, usually not more than one being other than an amino acid. The molecule will have 1 center of symmetry, being palindromic about the center of symmetry.

For the most part, the oligopeptide will have the following formula:

$$\left| \begin{array}{l} ZNH{-}Cys{-}Thr{-}Lys{-}Pro{-}AA^1{-}AA^2{-}AA^3{-}AA^4{-}AA^5{-}(Z^1){-}CO_2B \\ \quad\quad\; | \\ \quad\quad\; S{-} \end{array} \right|_2$$

wherein:

$AA^{1-5}$ are amino acids, which may be the same or different from the amino acids 143–147 of HBsAg or amino acids capable of immunologically mimicking the naturally occurring amino acids at those positions, wherein $AA^4$ and $AA^5$ may be bonds, the specific definitions of $AA^{1-5}$ to be defined subsequently;

$Z^1$ is a bond or a chain of amino acids of from 1 to 6, usually from 1 to 2 amino acids, which amino acids are the amino acids 148 to 153 of HBsAg or amino acids capable of immunologically mimicking such amino acids, but is preferably a bond;

Z is hydrogen or an amino acid or sequence, particularly the amino acids 134–138 of HBsAg, preferably hydrogen;

B is hydrogen or an alcoholic residue which is either lower alkyl or a group forming an ester capable of forming a peptide bond with a polypeptide in an aqueous medium. Illustrative groups include N-hydroxy succinimide, para-nitrophenol, and 4-hydroxy-3-nitrobenzenesulfonic acid.

For the most part, not more than 3, usually not more than 2 and preferably not more than about 1 of the amino acid units in each leg will differ from the naturally occurring sequence in HBsAg from amino acids 138 to 152.

For the most part, $AA^1$ will be a moderately polar amino acid, such as threonine, serine, and methionine, particularly threonine. $AA^2$ will be an acidic amino acid, such as aspartic or glutamic acid, particularly aspartic acid. $AA^3$ will be a neutral amino acid having hydrogen or a hydrocarbon group of from about 1 to 2 carbon atoms at the α carbon atom, being glycine, alanine, or α aminobutyric acid, $AA^4$ will be a polar amino acid, having a carboxamido group, being asparagine or glutamine, particularly asparagine. $AA^5$ will be cysteine or preferably a neutral or hydrophobic amino acid, having hydrogen or lower alkyl group of from about 1 to 3 carbon atoms at the α carbon atom, that is, being glycine, alanine α aminobutyric acid, or valine. Substantial variability appears to be permitted at $AA^5$.

Normally, the amino acids will have the natural L-configuration.

For the most part, the compounds of the subject invention will have the following formula:

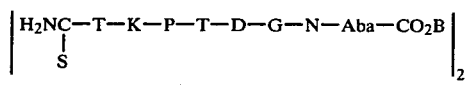

wherein:

B has been defined previously. The letters define the naturally occurring amino acids as set forth below:

C—cysteine
T—threonine
K—lysine
P—proline
D—aspartic
G—glycine
N—asparagine and Aba is α-aminobutyric acid.

The compounds of the subject invention find use as conjugates with antigens to provide immunogen conjugates which may serve as vaccines or for the production of antibodies which may find use in a wide variety of applications. Depending upon the purpose of the conjugate, a large variety of antigenic materials may be used. Where one is primarily concerned with the production of antibodies, popular antigens include bovine serum albumin, keyhole limpet hemocyanin, bovine gamma globulin, egg ovalbumin, ocular lens proteins, serum proteins, lipoproteins, synthetic proteins, and the like. Where a vaccine is to be employed, desirably the antigen will have been previously introduced into the hose, as a result of a natural phenomenon or by vaccination. Using this antigen, an haptenic site from a pathogen may be conjugated to the antigen for production of an effective vaccine for the pathogen.

The number of haptens conjugated to the antigen will vary widely, there being on the average at least 1 and not more than about 1 per 500 molecular weight, usually not more than about 1 per 5000 molecular weight, varying widely depending upon the molecular weight of the antigen and the purpose for the conjugate. The particular site of attachment between the hapten and antigen may vary widely, being the terminal carboxyl, the terminal amino (referring to an individual leg of the dimer) or an intermediate functionality. The site is not a critical factor of this invention and any of the groups may serve to provide for peptide bond formation.

If a specific site of attachment is desired, there are a wide variety of techniques to provide for activation at a particular site. For example, in preparing the oligopeptide, a selective protective group may be employed for a particular amino acid. For example, the aspartic acid group may be protected, so that upon cleavage of the terminal carboxy from the resin, the terminal carboxy will be free for activation, while the internal carboxy is still protected. One may then conjugate at the terminal carboxylic group using a carboxylic acid activating reagent e.g. carbodiimide, or prepare an activated ester using carbodiimide, followed by conjugation to the antigen and removal of the carboxyl protective group. Alternatively, amino groups may be selectively protected, so as to allow for conjugation at an amino site, particularly where the antigen has a large number of carboxyl groups e.g. tetanus toxoid. In many instances, the dimer and antigen may be combined at a molar ratio of about 1–200:1 with a water soluble carbodiimide and relatively random sites of attachment permitted. The amount of carbodiimide based on dimeric oligopeptide may vary from stoichiometric to about 20 fold excess or more.

For a description of oligopeptide synthesis using selective blocking groups, see Barany and Merrifield, Solid-Phase Peptide Synthesis, "The Peptides, Analysis, Synthesis, Biology," Special Methods in Peptide Synthesis, Part A, Vol. 2, Gross and Meienhofer eds., Academic Press, New York, 1980, pages 1–284; Chang et al., Int. J. Peptide Protein Research (1980) 15:485–494; Meienhofer et al., ibid (1979) 13:35–42.

The immunogen conjugates may be used in conventional ways for the production of antibodies. For the most part, the immunogen conjugate will be injected into any of a wide variety of vertebrates, particularly mammals, and an injection schedule provided so as to hyperimmunize the host. Blood may then be collected, the globulin fraction isolated and used as a mixture or purified by affinity chromatography. Alternatively, rather than polyclonal antibodies, monoclonal antibodies can be prepared by immunizing an appropriate host and by using the now classical Milstein-Kohler procedure, monoclonal antibodies specific for the hapten can be prepared.

Alternatively or in combination with the conjugation of the dimeric oligopeptide to the antigen, the oligopeptide may be oligomerized to oligomers having at least three units and may have 10 or more. The oligomers may be used as immunogens by themselves or in combination with the immunogen conjugate. Conveniently, by using an activating group, such as carbodiimide, oligomers and immunogen conjugates may be prepared simultaneously. Desirably, high concentrations of the various components may be used, usually the carbodiimide and oligopeptide being greater than about 0.1M.

The haptens of the subject invention can also be used as reagents in diagnostic assays for HBV or antibodies to HBV in physiological fluids. By conjugating the subject haptens to a wide variety of labels, the resulting conjugates can be used in conjunction with the antibodies for detection of HBV or the labeled hapten may be used directly for the determination of the presence of antibodies to the a determinant of HBsAg. Various labels include radionuclides, fluorescers, chemiluminescers, enzymes, particles, enzyme substrates and cofactors, and the like. A large number of patents as well as literature articles are available describing a wide variety of reagents and protocols which may be employed with the haptens of the subject invention for detection of HBV or receptors to HBV. See for example, U.S. Pat. Nos. 3,690,834; 3,817,837; 3,935,074; 4,233,402 and 4,318,980.

The haptens of this invention may be prepared in conventional ways. Particularly they may be prepared employing solid phase synthesis of oligopeptides. Description of various techniques may be found in U.S. Pat. No. 4,127,526; in the Peptides, Proceedings of the Fifth American Peptide Symposium, Goodman and Meienhofer, eds., John Wiley & Sons, New York; Barany and Merrifield, Solid-Phase Peptide Synthesis, "The Peptides, Analysis, Synthesis, Biology," Special Methods in Peptide Synthesis, Part A, vol. 2, Gross and Meienhofer, eds., Academic Press, New York, N.Y. 1980. Conveniently, where there is only one cysteine group, mild oxidation can be employed to provide the dimer, e.g. aqueous ferricyanide or air.

When used as a vaccine, the manner of application of the immunogen conjugate and/or oligomer may be varied widely. Any of the conventional methods for administration of a dead vaccine are applicable. These include oral application on a solid physiologically acceptable base or in a physiologically acceptable dispersion, parenterally, by injection, or the like. The dosage of the vaccine will depend on the route of administration and will vary according to the size of the host. Because the vaccine has few, if any, side effects, relatively large dosages may be used without injury to the host. Normally, the amount of the vaccine will be from about 1 $\mu$g to 20 mg per kilogram of host, more usually from about 5 $\mu$g to 2 mg given subcutaneously or intramuscularly after mixing with an appropriate carrier or an adjuvant to enhance immunization with the vaccine.

Various methods of achieving adjuvant effect for the vaccine include use of agents such as aluminium hydroxide or phosphate (alum), commonly used as 0.05 to 0.1 percent solution in phosphate buffered saline, admixture with synthetic polymers of sugars (Carbopol) used as 0.25 percent solution mixture with bacterial cells such as C. parvum or endotoxins or lipopolysaccharide components of Gram-negative bacteria, emulsion in physiologically acceptable oil vehicles such as mannide mono-oleate (Aracel A) or emulsion with a 20 percent solution of a perflurocarbon (Fluosol-DA) used as a blood substitute.

As the antigen of particular interest for vaccines are bacterial toxins against which the host has been preimmunized, for example, tetanus toxoid or diphtheria toxoid, particularly having one oligopeptide group per 500 to 10,000 daltons of the antigen.

The amount of the adjuvant which is employed will vary widely depending upon the nature of the adjuvant, generally varying from 0.1 to 100 times the weight of the immunogen conjugate, more usually from about 1 to 10 times.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for HBV. The assays may be performed by labelling the oligonucleotide dimer with conventional labels, such as described previously.

Radioimmunoassays are illustrative of the heterogeneous assays. A radioimmunoassay could be performed by binding the oligonucleotide dimer to a surface, either a particle or the surface of a container, adding the serum sample to the bound dimer, and allowing the mixture to incubate for sufficient time for any antibody to dimer to react with the bound dimer. One would then add radionuclide-labelled dimer to the container, incubate for a period of time sufficient for the labelled dimer to bind any antibody bound to the surface, wash, and then measure the radioactivity bound to the surface. Alternative protocols may be employed.

The following examples are offered by way of illustration and not by way of limitation.

The dimeric nonapeptide compound of the formula:

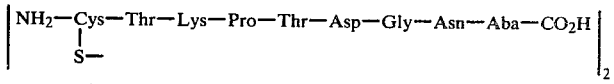

was prepared in accordance with conventional ways. The procedure described by Stewart and Young, Solid Phase Peptide Synthesis, W. H. Freeman and Co., San Francisco, CA., pp.1ff, was employed. Chloromethyl resin was used as the solid phase support and t-butyloxycarbonyl protected amino acids added stepwise. The oligopeptide was cleaved by mild HF treatment (0.1×usual HF concentration) which also provided for deprotection. (Bhatnagar et al. (1981) in Peptides, Proceedings of the Seventh American Peptide Symposium, eds. Rich, D. H. and Gross, E. (Pierce Chemical Co., Rockford, Ill., pp. 97–100).

The procedure involved after each coupling in a semi-automatic apparatus successive washes (5× each) with $CH_2Cl_2$, DMF and $CH_2Cl_2$, swelling the resin and washing with $CH_2Cl_2$, deprotecting with $CH_2Cl_2$:trifluoroacetic acid (1:1) (2×15 min), followed by washings with $CH_2Cl_2$ (2×), dioxane-$CH_2Cl_2$ (1:1; 5×) and DMF (5×). Neutralization employed DMF:$Et_3N$ (9:1) (2×10 min; 1×5 min), followed by washings (5× each) with DMF and $CH_2Cl_2$.

After the oligopeptide was prepared, it was cleaved from the resin and deprotected using HF as indicated above, followed by solution in PBS. On standing, the oligopeptide dimerized and the dimer was separated from the monomer using P-2 gel filtration with PBS as the eluent, the dimer being in the earlier fractions.

The dimer was then used for conjugation employing 20 mg of the dimer, 20 mg of the antigen and 20 mg of ethyl dimethylaminopropyl carbodiimide in one ml PBS at room temperature for 16 hr. The mixture was then exhaustively dialysed with PBS to remove low molecular weight materials.

For immunization, each conjugate (50 $\mu$g) was mixed (1 ml) with complete Freund's adjuvant for the first injection and incomplete Freund's adjuvant for subsequent injections and injected intramuscularly thrice at monthly intervals into 7 rabbits ($\alpha$-1 to $\alpha$-7), previously immunized (primed) with tetanus toxoid (T.T.). Three rabits ($\alpha$-1 to $\alpha$-3) immunized with the monomeric nonapeptide coupled to T.T. through the amino-terminus using a succinic acid bridge produced poor or no immune response. In contrast, four rabbits ($\alpha$-4 to $\alpha$-7) immunized with dimeric nonapeptide conjugated with T.T. as described above showed high immunogenicity exceeding an RIA ratio of 10 (Francis, et al., Annals of Internal Medicine (1982) 97:362–366; MMWR June 25, 1982, 31:317–321) which is considered unequivocal evidence of immunity to HBV infection in humans. The UC rabbits (UC-1 and UC-5) had a relatively poor immune response to the monomeric nonapeptide coupled to keyhole limpet hemocyanin (KLH) (Bhatnagar et al., PNAS USA (1982) 79:4400–4404.) Hyperimmunization of UC-5 with dimeric nonapeptide (coupled to KLH by the carbodiimide reaction) produced a better immune response than hyperimmunization of UC-1 with monomeric nonapeptide (coupled to KLH through the amino-terminus by activation on solid-phase). The RIA rato of 54.9 in UC-5 is the highest yet achieved by any synthetic peptide analogue of HBsAg tested so far in any laboratory. This extremely vigorous immune response was obtained only after the fourth immunization (see Table below):

RESULTS OF RABBITS IMMUNIZED WITH DIMERIC FORM OF CYS—THR—LYS—PRO—THR—ASP—GLY—ASN—ABA

| Rabbit # | Primed with | Immunized with | Anti-HBsAg Preimmuniz | (P/N Ratio)* Postimm. |
|---|---|---|---|---|
| α-1 | T.T. | T.T. —CONH (139-146-Aba) | 1.4 | 2.3 |
| α-2 | T.T. | T.T. —CONH (139-146-Aba) | 6.8 | 1.8 |
| α-3 | T.T. | T.T. —CONH (139-146-Aba) | 0.9 | 3.0 |
| α-4 | T.T. | $(139\text{-}146\text{-}Aba)_2$-T.T. | 1.1 | 12.0 |
| α-5 | T.T. | $(139\text{-}146\text{-}Aba)_2$-T.T. | 1.2 | 19.2 |
| α-6 | T.T. | $(139\text{-}146\text{-}Aba)_2$-T.T. | 2.0 | 8.7 |
| α-7 | T.T. | $(139\text{-}146\text{-}Aba)_2$-T.T. | 1.7** | 3.7 |
| UC-1 | KLH-139-147 | KLH—CO—NH—(139-146-Aba) | 1.2 | 15.9*** |
| UC-5 | 139-147-KLH | $(139\text{-}146\text{-}Aba)_2$—KLH | 2.0 | 54.9*** |

*A ratio unit of <2.1 is considered positive in the standard Ausab test.
**The lowest P/N ratio of an early postimmunization specimen of the α-7 rabbit was used in lieu of unavailable preimmunization serum.
***Prior to the fourth immunization the P/N ratio was less than 10.

It is evident from the above data, that the subject oligopeptide dimers provide for highly active effective vaccines in mammals providing for a strong immune response. Thus, high yields of antibodies can be obtained having high specificity, which may then be used in diagnosis and treatment. Therefore, the subject invention provides a simple, convenient method for making relatively small oligopeptides, which can readily be made by synthetic procedures, which may be used as reagents in diagnostic assays, for conjugation to antigens, particularly bacterial antigens previously used as vaccines, for use as vaccines against hepatitis and for the production of antibodies which may also find use as reagents and for use in passive immunization.

Although the foregoing invention has been described in some detail by way of illustration and example for purposes of clarity of understanding, it will be obvious that certain changes and modifications may be practiced within the scope of the appended claims.

What is claimed is:

1. The dimeric nonapeptide compound of the formula:

$$|H_2N-\underset{\underset{S}{|}}{Cys}\text{-}Thr\text{-}Lys\text{-}Pro\text{-}Thr\text{-}Asp\text{-}Gly\text{-}Asn\text{-}Aba\text{-}CO_2B|_2$$

wherein: B is hydroxyl or the residue of an hydroxylic compound which provides an ester which forms amide bonds with polypeptides in aqueous media.

2. A compound according to claim 1, wherein B is hydroxyl.

3. A compound according to claim 1, wherein hydroxylic compound which provides an ester is selected from the group consisting of N-hydroxy succinimide, para-nitrophenol and 4-hydroxy-3-nitrobenzenesulfonic acid.

* * * * *